United States Patent
Muffoletto et al.

(10) Patent No.: US 9,824,829 B1
(45) Date of Patent: Nov. 21, 2017

(54) CAPACITOR HAVING MULTIPLE ANODES HOUSED IN A SWAGED CASING

(71) Applicant: Greatbatch Ltd., Clarence, NY (US)

(72) Inventors: Barry C. Muffoletto, Alden, NY (US); Anthony C. Perez, Wheatfield, NY (US)

(73) Assignee: Greatbatch Ltd., Clarence, NY (US)

( * ) Notice: Subject to any disclaimer, the term of this patent is extended or adjusted under 35 U.S.C. 154(b) by 0 days.

(21) Appl. No.: 15/467,254

(22) Filed: Mar. 23, 2017

(51) Int. Cl.
  *H01G 11/80* (2013.01)
  *H01G 11/52* (2013.01)
  *H01G 11/46* (2013.01)

(52) U.S. Cl.
  CPC ............ *H01G 11/80* (2013.01); *H01G 11/46* (2013.01); *H01G 11/52* (2013.01)

(58) Field of Classification Search
  None
  See application file for complete search history.

(56) References Cited

U.S. PATENT DOCUMENTS

| | | | |
|---|---|---|---|
| 5,926,362 A * | 7/1999 | Muffoletto | H01G 9/04 361/503 |
| 6,334,879 B1 | 1/2002 | Muffoletto et al. | |
| 6,850,405 B1 * | 2/2005 | Mileham | A61N 1/375 29/25.41 |
| 7,072,171 B1 | 7/2006 | Muffoletto et al. | |
| 7,483,405 B2 | 1/2009 | Emond et al. | |
| 8,027,149 B2 | 9/2011 | Hahl et al. | |
| 9,514,886 B1 * | 12/2016 | Kaiser | B02C 19/186 |
| 9,721,730 B1 * | 8/2017 | Muffoletto | H01G 9/08 |

* cited by examiner

Primary Examiner — Dion R Ferguson
(74) Attorney, Agent, or Firm — Michael F. Scalise

(57) ABSTRACT

A capacitor is described. A casing for the capacitor comprises a container having a face wall joined to a surrounding sidewall extending to a annular edge defining an open end of the container. An inwardly extending protrusion is located intermediate the face wall and the annular edge at the container open end. A partition plate is supported on the protrusion to thereby provide a first capacitor enclosure bounded by the face wall, the surrounding sidewall and the partition plate. A cover plate is secured to the annular edge to close the open end of the container and provide a second capacitor enclosure bounded by the partition plate, the surrounding sidewall and the cover plate. An anode, for example of tantalum, and a cathode active material, for example of ruthenium oxide, reside in capacitive association with each other inside each of the first and second capacitor enclosures. A working electrolyte is also contained in the capacitor enclosures. Finally, leads extend from each anode through insulative seals structures supported by the casing for making electrical connection to the capacitor.

16 Claims, 3 Drawing Sheets

CAPACITOR HAVING MULTIPLE ANODES HOUSED IN A SWAGED CASING

FIELD OF THE INVENTION

The present invention relates to capacitors, more particularly, to a casing structure designed to house at least two anodes for an electrolytic capacitor.

SUMMARY OF THE INVENTION

As more and more medical applications are investigated and implemented to aid and assist the human body, devices needed to deliver the desired therapy are becoming increasingly more sophisticated, both functionally and in terms of their structural makeup. Modern implantable devices require power sources that are relatively small in size, but powerful enough to meet the therapy requirements. For example, a cardiac defibrillator has a battery powering circuits performing such functions as, for example, the heart sensing and pacing functions. This requires electrical current of about 1 microampere to about 100 milliamperes. From time-to-time, the cardiac defibrillator may require a generally high rate, pulse discharge component that occurs, for example, during charging of a capacitor assembly in the defibrillator for the purpose of delivering an electrical shock to the heart. The electrical shock is for the purpose of treating a tachyarrhythmia, the irregular, rapid heartbeats that can be fatal if left uncorrected. Treating a tachyarrhythmia requires electrical current of about 1 ampere to about 4 amperes to be drawn from the battery to sufficiently charge the capacitor assembly.

The current trend in medicine is to make cardiac defibrillators, and like implantable devices, as small and lightweight as possible without compromising their power. This, in turn, means that the components within the capacitor, particularly the anode, need to be constructed to optimum energy density and volumetric efficiency parameters.

The present invention is, therefore, directed to a novel casing design for a capacitor. The capacitor casing houses at least two anodes in a volumetrically efficient design comprising an open-ended container having a sidewall provided with at least one inwardly extending protrusion. The protrusion can be annularly endless or discontinuous at spaced locations around an inner perimeter of the sidewall. The protrusion supports a partition plate to thereby provide a first capacitor enclosure for housing an anode and associated cathode active material therein. A cover plate closes the open-ended container to thereby provide a second capacitor enclosure, which likewise houses an anode and cathode active material capacitively associated with each other. If desired, the container can be provided with additional inwardly extending protrusions supporting respective partition plates to provide as many capacitor enclosures for housing anode/cathode active material assemblies as needed for a particular application.

The cathode active material is, for example, ruthenium oxide while the anode typically comprises an anode active material such as tantalum, aluminum, or niobium. There is also a separator intermediate the anode and cathode in both of the first and second capacitor enclosures.

Electrical connection to the capacitor is made through a first insulative seal supported by the container and a second insulative seal supported by at least one of the container and the cover plate. The insulative seals electrically insulate a respective first lead for the first anode housed in the first capacitor enclosure and a second lead for the second anode housed in the second capacitor enclosure from the casing serving as a terminal for the cathode active material. Finally, a working electrolyte is provided in the first and second capacitor enclosures in contact with the first and second anodes and the cathode active material.

Thus, the present capacitor embodiments provide the designer with form factors that are readily adaptable for powering modern implantable medical devices.

These and other objects of the present invention will become increasingly more apparent to those skilled in the art by reference to the following detailed description and the appended drawings.

DETAILED DESCRIPTION OF THE PREFERRED EMBODIMENTS

Figure 1:
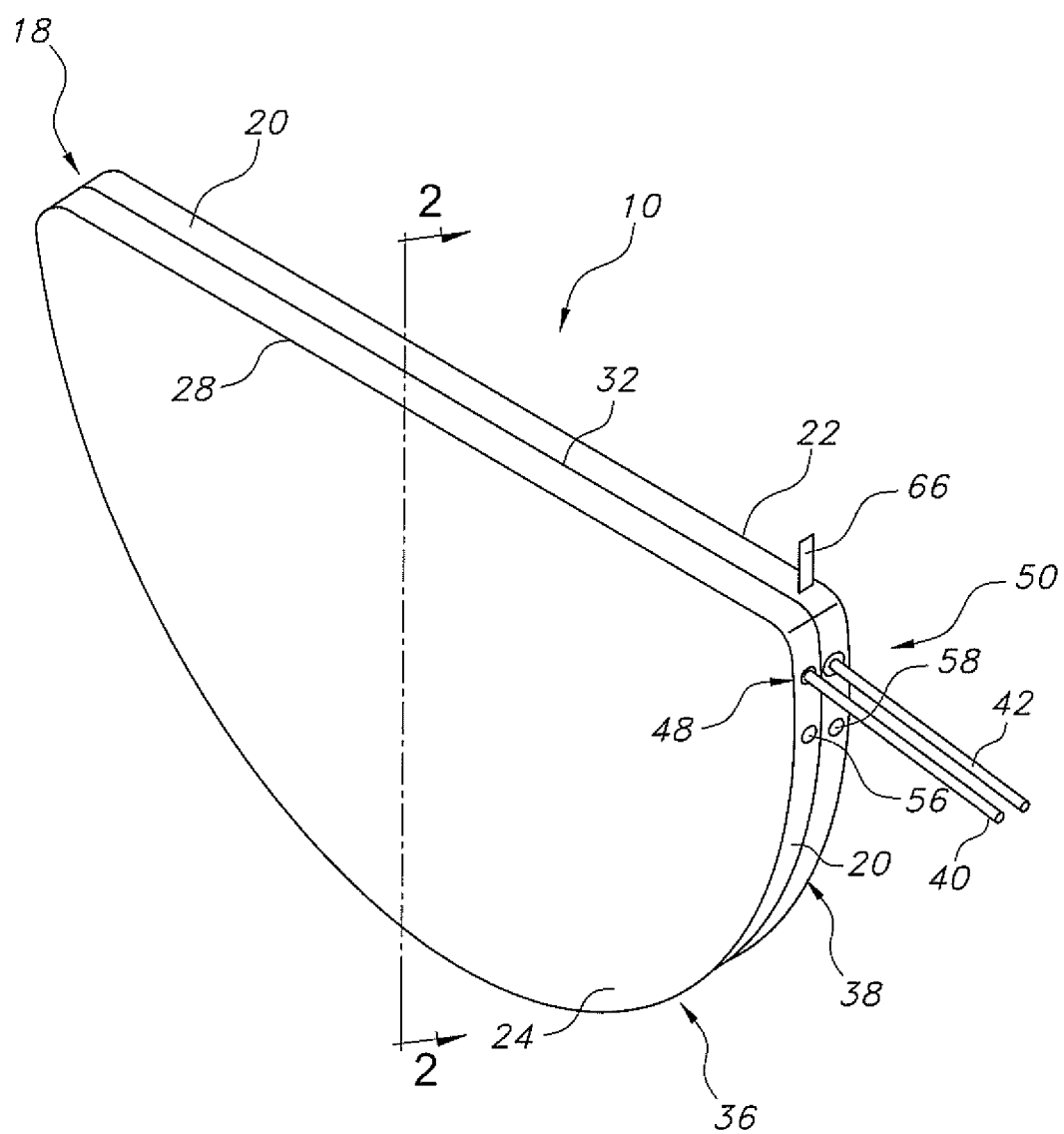
FIG. 1 is a perspective view of an exemplary capacitor 10 according to the present invention.
Figure 2:
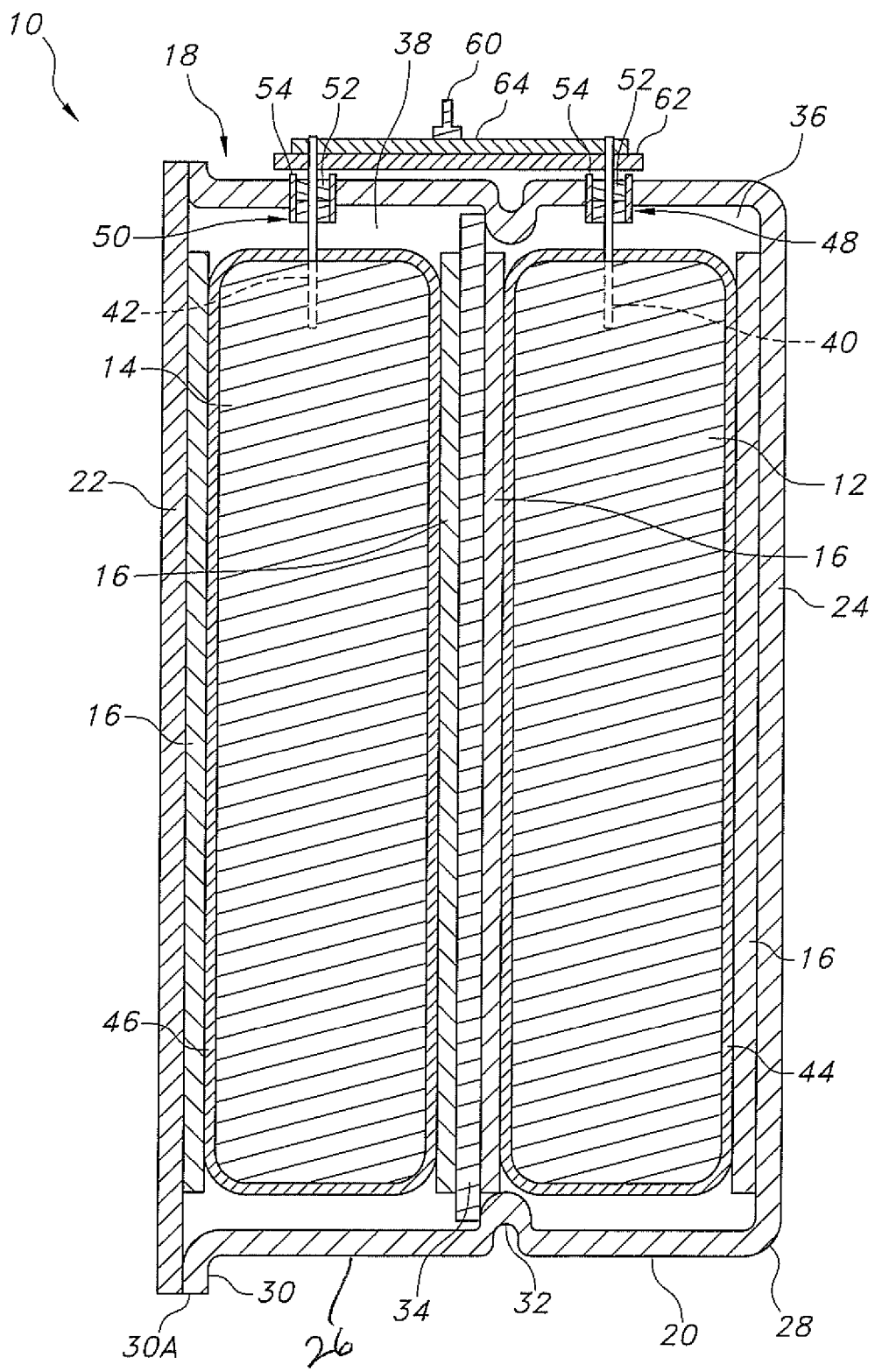
FIG. 2 is a cross-sectional view taken along line 2-2 of FIG. 1 illustrating a dual anode design with each anode housed in a respective capacitor enclosure.

Referring now to the drawings, an exemplary capacitor 10 according to the present invention is illustrated in FIGS. 1 and 2. As will be described in detail hereinafter, capacitor 10 is well suited for implantable cardiac device capacitor applications and comprises a first anode 12 of a first anode active material, a second anode 14 of a second anode active material, and a cathode of a cathode active material 16, all housed inside a hermetically sealed casing 18. Preferably, the side-by-side first and second anodes 12, 14 are of the same active material. The capacitor 10 can be of either an electrochemical type with the anode and the cathode being provided by conductive substrates having a capacitive material contacted thereto or, an electrolytic type with the cathode being provided by a conductive substrate having capacitive properties and the anode being of a valve metal. The illustrated capacitor 10 is preferably of the latter type, however, that should not be construed as limiting. The capacitor electrodes are operatively associated with each other by a working electrolyte (not shown) contained inside the casing 18.

Exemplary casing 18 is of a metal material and comprises an open ended container 20 closed by a lid or cover plate 22. The container 20 is, for example, a shallow-drawn member, a metal injection molded member, or a member machined from a block of suitable metal, and comprises a face or bottom wall 24 joined to a surrounding sidewall 26 by a radiused intermediate wall 28. Surrounding sidewall 26 extends to an upper outwardly extending rim 30 having an edge 30A defining the open end of the container 20. Moreover, the surrounding sidewall 26 includes an inwardly extending protrusion 32 that resides about mid-way between the face wall 24 and the rim 30. A preferred method of forming the protrusion 32 is by a swaging process, which is a forging process in which the dimensions of the sidewall 26 are altered using dies into which the sidewall is forced. Swaging is usually a cold working process; however, it is sometimes done as a hot working process. The protrusion 32 can be an endless annular structure or it can be discontinuous, residing at spaced locations along a perimeter of the surrounding sidewall 26.

An internal partition plate 34 is supported on the protrusion 32, preferably on a side thereof so that the protrusion resides between the plate 34 and face wall 24. If desired; however, the partition plate 34 is supported on the protrusion 32 so that the plate is intermediate the protrusion and the face wall 24. In any event, the partition plate 34 is secured in place secured to the protrusion 32, whether endless or discontinuous, by a weld, preferably by laser or resistance spot welding (not shown).

Lid 22 or cover plate is a plate-shaped member that is supported on the rim 30 to thereby close the open end of the container 20. Preferably, the outer edge of the cover plate 22 is aligned with the edge 30A of the outwardly extending rim 30. While not shown in the drawings, the cover plate 22 is secured to the rim 30 by a weld, which is preferably a laser weld.

In that manner, the casing 18 provides a first capacitor enclosure 36 delineated as the area bounded by the face wall 24, surrounding sidewall 26 and partition plate 34, and a second capacitor enclosure 38 delineated as the area bounded by the partition plate 34, surround sidewall 26 and cover plate 22.

The container 20, cover plate 22 and partition plate 34 are made of a conductive metal selected from the group consisting of tantalum, titanium, nickel, niobium, stainless steel, aluminum, zirconium, and mixtures and alloys thereof. Regardless the metal, the container 20, cover plate 22 and partition plate 34 each have a thickness of about 0.015 to about 0.5 millimeters and when assembled together as the casing 18 serve as one terminal or contact for making electrical connection between the capacitor 10 and its load.

The cathode active material 16 is contacted to an inner surface of the face wall 24 of the container 20. Cathode active material 16 is also supported on the opposed lower and upper major surfaces of the partition plate 34 (the lower surface facing the face wall 24 and the upper surface facing the opposite direction). Prior to securing the partition plate 34 to the protrusion 32, the first anode 12 in the form of a pressed valve metal pellet, preferably of tantalum, that has been sintered, anodized and subjected to a formation protocol, is housed in the open first capacitor enclosure 36. When so housed, the anode 12 is adjacent to, but spaced from the cathode active material 16 coating the face wall 24. The partition plate 34 is then secured to the protrusion 32 to close the first capacitor enclosure 36. While not shown in the drawings, the partition plate 34 is preferably perforated where it supports cathode active material 16.

The second anode 14 in the form of a pressed valve metal pellet, preferably of tantalum, that has been sintered, anodized and subjected to a formation protocol, is next housed in the open-ended second capacitor enclosure 38. When so housed, the anode 14 is adjacent to, but spaced from the cathode active material 16 coating the upper surface of the partition plate 34. With cathode active material 16 coating an inner surface of the cover plate 22, the cover plate is then secured to the rim 30 to close the second capacitor enclosure 38. Preferably, the various coatings of cathode active material 16 are substantially aligned in a face-to-face relationship with the major faces of the anodes 12, 14.

The active material of the anodes 12 and 14 is typically of a metal in the form of a pellet. The anode metal is selected from the group of valve metals consisting of tantalum, aluminum, titanium, niobium, zirconium, hafnium, silicon, germanium, and mixtures thereof. As is well known by those skilled in the art, the anode metal in powdered form, for example tantalum powder, is compressed into a pellet having an anode lead (lead 40 for anode 12 and lead 42 for anode 14) embedded therein and extending there from, and sintered under a vacuum at high temperatures. The porous body is then anodized in a suitable electrolyte to fill its pores with electrolyte and form a continuous dielectric oxide film on the sintered body. A preferred tantalum material and method of manufacturing an anode pellet for the present capacitor 10 is described in U.S. Pat. No. 9,312,075 to Liu et al., which is assigned to the assignee of the present invention and incorporated herein by reference.

In particular, the anode pellets 12, 14 and their leads 40, 42 are anodized by immersing the pellet/lead assembly in an electrolyte and applying a current. The anodizing electrolyte includes constituents such as water and phosphoric acid and perhaps other organic solvents. The application of current drives the formation of an oxide film that is proportional in thickness to the targeted forming voltage. A pulsed formation process may be used where current is cyclically applied and removed to allow diffusion of heated electrolyte from the internal pores of the anode. Intermediate washing and annealing steps may be performed to facilitate formation of a stable, defect free oxide. Preferably, the leads 40, 42 are of the same material as the anodes 12, 14, and the anode pellet/lead assembly is anodized to a formation voltage that is greater than zero up to 550 V.

Preferably the various cathode active material 16 coatings (contacting the inner surface of face wall 24, both major sides or surfaces of the partition plate 34, and the inner surface of cover plate 22) have a thickness of about a few hundred Angstroms to about 0.1 millimeters and are aligned in a face-to-face relationship with the immediately adjacent major faces of the anodes 12, 14. Alternatively, the cathode active material 16 is coated on a conductive substrate (not shown) in electrical contact with the inner surface of face wall 24, both major sides or surfaces of the partition plate 34, and the inner surface of cover plate 22. In any event, the cathode active material 16 is preferably spaced from the surrounding sidewall 20.

In that respect, the face wall 24, partition plate 34, and the cover plate 22 may be of an anodized-etched conductive material, have a sintered active material with or without oxide contacted thereto, or they may be contacted with a double layer capacitive material, for example a finely divided carbonaceous material such as graphite, carbon, activated carbon, platinum black, a redox, pseudocapacitive or an under potential material, or they may be an electroactive conducting polymer such as polyaniline, polypyrrole, polythiophene, and polyacetylene, and mixtures thereof.

According to one preferred aspect of the present invention, the redox or cathode active material 16 includes an oxide of a first metal, the nitride of the first metal, the carbon nitride of the first metal, and/or the carbide of the first metal, the oxide, nitride, carbon nitride, and carbide having pseudocapacitive properties. The first metal is preferably selected from the group consisting of ruthenium, cobalt, manganese, tantalum, iron, niobium, iridium, titanium, zirconium, hafnium, rhodium, vanadium, osmium, palladium, and platinum.

The cathode active material 16 may also include a second or more metals. The second metal is in the form of an oxide, a nitride, a carbon nitride or a carbide, and is not essential to the intended use of the conductive face wall 24 of container 20, partition plate 34, and cover plate 22 as a capacitor electrode. The second metal is different than the first metal and is selected from one or more of the group consisting of tantalum, titanium, nickel, iridium, platinum, palladium, gold, silver, cobalt, molybdenum, ruthenium, manganese, tungsten, iron, zirconium, hafnium, rhodium, vanadium, osmium, and niobium. In a preferred embodiment of the present invention, the cathode active material 16 includes an oxide of ruthenium and is substantially devoid of the second or more metals.

The cathode active material 16 may also be selected from graphitic or glassy carbon on titanium carbide, carbon and silver vanadium oxide on titanium carbide, carbon and crystalline manganese dioxide on titanium carbide, platinum on titanium, ruthenium on titanium, barium titanate on titanium, carbon and crystalline ruthenium oxide on titanium carbide, carbon and crystalline iridium oxide on titanium carbide, silver vanadium oxide on titanium, and activated carbon.

As disclosed in U.S. Pat. No. 7,116,547 to Seitz et al., a preferred cathode material coating process is by pad printing. An ultrasonically generated aerosol, as described in U.S. Pat. Nos. 5,894,403, 5,920,455, 6,224,985, and 6,468,605, all to Shah et al., is also suitable for making a coating of the cathode active material 16. In that manner, the ultrasonically generated cathode active material contacted to the conductive inner surface of face wall 24, both major conductive surfaces of the partition plate 34 and the conductive inner surface of cover plate 22 has a majority of its particles with diameters of less than about 10 microns. This provides an internal surface area for the active material of about 10 $m^2$/gram to about 1,500 $m^2$/gram. The Shah et al. '403, '455, '985 and '605 patents and the Seitz et al. '547 patent are assigned to the assignee of the present invention and incorporated herein by reference.

As shown in FIG. 2, to prevent an internal electrical short circuit between the electrodes, a first separator envelope 44 of electrically insulative material surrounds the first anode 12 and a second separator envelope 46 of electrically insulative material surrounds the second anode 14. The separator envelopes 44, 46 prevent direct physical contact of the respective anodes 12, 14 with the facing cathode active materials 16 while allowing for ionic transport during charging and discharging of the capacitor 10. The respective separator envelopes 44, 46 are of materials that are chemically unreactive with the anode and cathode active materials and both chemically unreactive with and insoluble in the electrolyte.

Illustrative separator materials include woven and non-woven fabrics of polyolefinic fibers including polypropylene and polyethylene, or fluoropolymeric fibers including polyvinylidene fluoride, polyethylenetetrafluoroethylene, and polyethylenechlorotrifluoroethylene laminated or superposed with a polyolefinic or fluoropolymeric microporous film, non-woven glass, glass fiber materials and ceramic materials. Suitable microporous films include a polyethylene membrane commercially available under the designation SOLUPOR®, (DMS Solutech); a polytetrafluoroethylene membrane commercially available under the designation ZITEX®, (Chemplast Inc.) or EXCELLERATOR®, (W. L. Gore and Associates); a polypropylene membrane commercially available under the designation CELGARD®, (Celgard LLC); and a membrane commercially available under the designation DEXIGLAS®, (C. H. Dexter, Div., Dexter Corp.). Cellulose based separators also typically used in capacitors are contemplated by the scope of the present invention. Depending on the working electrolyte, the material used for the envelopes 44, 46 can be treated to improve its wettability, for example with a surfactant, as is well known by those skilled in the art. The working electrolyte will be described in detail hereinafter.

The capacitor 10 illustrated in FIGS. 1 and 2 further includes an insulator and seal structure, for example a glass-to-metal seal, for each of the anodes 12, 14 and their leads 40, 42. The respective insulator and seal structures are designated 48 and 50 in the drawings. As is well known to those skilled in the art, the insulator and seal structures 48 and 50 comprise an insulative glass 52 that provides a hermetic seal between the inside of a ferrule 54 supported by the casing sidewall 20 and the anode leads 40, 42. The insulative glass 52 is, for example, ELAN® type 88 or MANSOL™ type 88. In that manner, those portions of the anode leads 40, 42 extending outside the casing 18 are hermetically sealed from the interior thereof to electrically isolate the leads from the first and second capacitor enclosures 36, 38 comprising the casing 18, which casing serves as the terminal for the cathode electrode. The ferrules 54 for the respective insulator and seal structures 48, 50 are configured for mounting in a suitably sized opening in the sidewall 20 of the casing 18 for the lead 40 of the first anode 12 and in an opening in either the surrounding sidewall 20 or cover plate 22 for the lead 42 of the second anode.

Alternatively, the insulator and seal structures 48, 50 do not have glass isolating the leads 40, 42 from the respective ferrules 54. Instead, the insulative material 52 is a synthetic elastomeric material that is configured to seal between feedthrough leads 40, 42 and their ferrules 54. A suitable synthetic elastomeric material is, for example, Master-Sil 151 made by Master Bond. While such a seal structure using only a synthetic polymeric material is not necessarily hermetic, acceptable isolation of the working electrolyte from inside the first and second capacitor enclosures 36, 38 to the outside the casing 18 is provided.

To complete the capacitor 10, a working electrolyte (not shown) is filled into the first and second capacitor enclosures 36, 38 to contact the anode 12, 14 and cathode active materials 16. A suitable working electrolyte for the capacitor 10 is described in U.S. Pat. No. 6,219,222 to Shah et al., which includes a mixed solvent of water and ethylene glycol having an ammonium salt dissolved therein. U.S. Patent Pub. Nos. 2003/0090857 and 2003/0142464 describe other working electrolytes for the present capacitor 10. The working electrolyte of the former publication comprises water, a water-soluble inorganic and/or organic acid and/or salt, and a water-soluble nitro-aromatic compound while the latter relates to a working electrolyte having de-ionized water, an organic solvent, isobutyric acid and a concentrated ammonium salt. These publications and patent are assigned to the assignee of the present invention and incorporated herein by reference.

Regardless its constituents, the working electrolyte is provided inside the hermetically sealed capacitor enclosures 36, 38 through respective fill openings, each opening closed by a hermetic closure 56 and 58 (FIG. 1), as is well known by those skilled in the art.

As shown in FIG. 1, the anode leads 40, 42 for capacitor 10 are unconnected from each other so that the respective anodes 12, 14 can be charged independently. This could take the form of charging one of the anodes partially or completely to a rated voltage, and then charging the other anode. In other situations, it might be preferred to charge one anode at a rate different than that at which the other anode is charged. For example, a pulse current could charge one of the anodes while the other is done by constant power charging. An advantage of separately connecting the anode leads 40, 42 to an external charging circuit is that charging and discharging currents can be distributed over the anodes 12, 14, which allows smaller, more flexible leads 40, 42 and connections than one lead with an equivalent current carrying capacity.

Alternatively, FIG. 2 illustrates that the anodes 12, 14 can be connected to a common polarity terminal. In that manner, the respective anode leads 40, 42 are electrically connected to a common positive polarity terminal 60. This is accomplished by first mounting an insulator 62 having spaced apart openings sized to receive the leads 40, 42. A bridge 64 of conductive material, for example, nickel, is then supported on the insulator 62. The bridge 64, which has a pair of openings that receive the anode leads 40, 42, is secured to these leads by respective welds, preferably by laser welds, (not shown) to electrically connect the leads together in parallel. Finally, the common positive terminal 60 is electrically connected to bridge 64. The bridge 64 can also be crimped onto the leads 40, 42 by applying a force that deforms the bridge from opposed directions.

In use, the capacitor 10 is connected to a load (not shown) as a power source. That can be done by either connecting the leads 40, 42 or the negative polarity terminal pin 60 to the load. A common positive terminal pin 66 (FIG. 1) connected to the casing 18 is also connected to the load to complete the electrical connection.

While not shown in the drawings, a molded polymeric cradle or restraint is preferably provided for containing the anodes 12, 14 in the desired position inside the capacitor enclosures 36, 38 should the capacitor 10 experience high shock and vibration conditions. Suitable restraints are described in U.S. Pat. No. 7,085,126 to Muffoletto et al. and U.S. Pat. No. 7,092,242 to Gloss et al., which are assigned to the assignee of the present invention and incorporated herein by reference.

Figure 3:
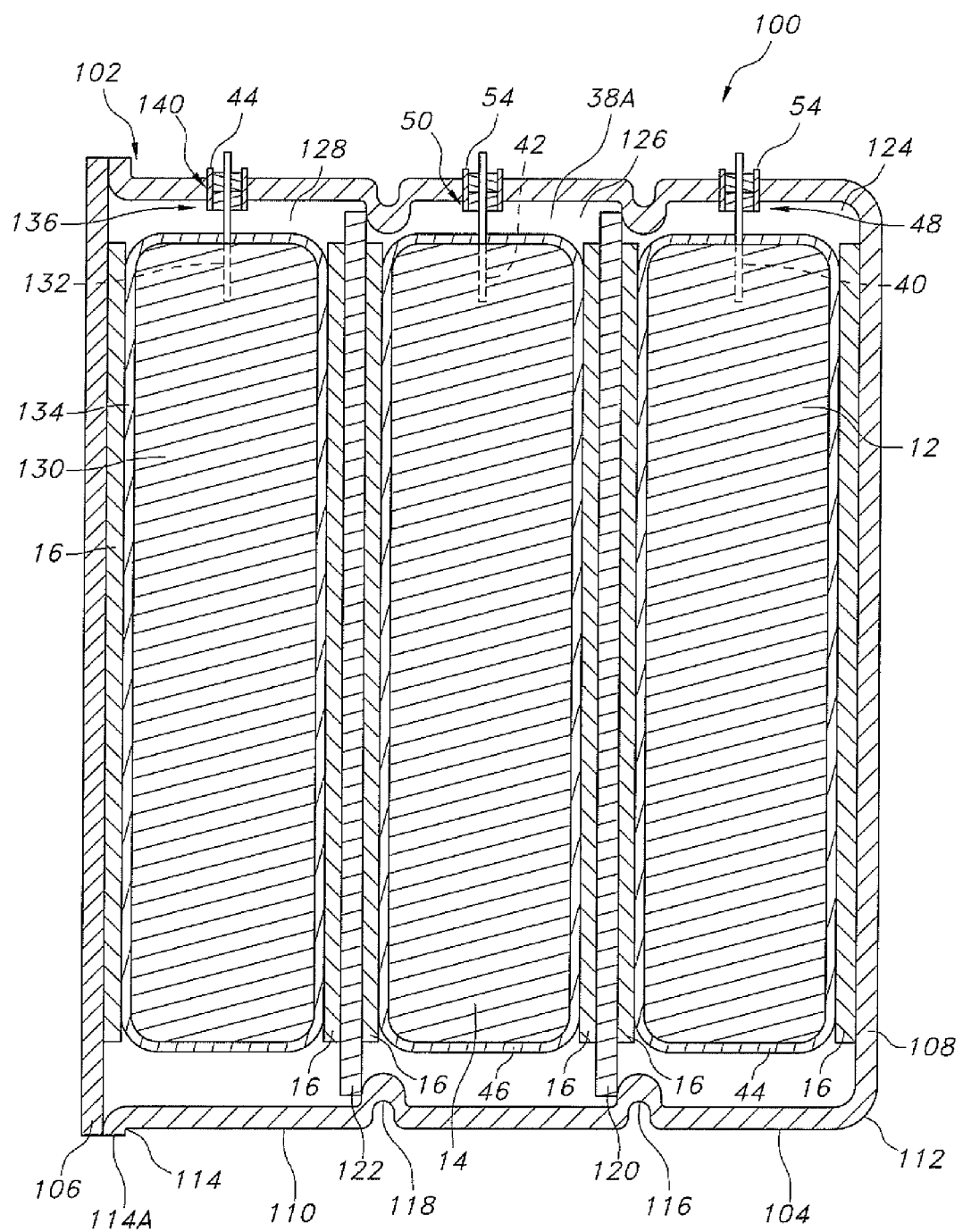
FIG. 3 is a partially broken-away view illustrating another casing embodiment for a three anode capacitor according to the present invention.

It should be understood that the capacitor 10 of the present invention is not limited to dual anode designs. FIG. 3 is a cross-sectional view of another embodiment of a capacitor 100 according to the present invention. Capacitor 100 has a casing 102 of a metal material, the casing comprising an open ended container 104 closed by a lid or cover plate 106. The container is similar to container 20 (FIG. 2) and is, for example, a shallow-drawn member, a metal injection molded member, or a member machined from a block of suitable metal. The container 104 comprises a face or bottom wall 108 joined to a surrounding sidewall 110 by a radiused intermediate wall 112. Surrounding sidewall 110 extends to an upper outwardly extending rim 114 having an edge 114A defining the open end of the container 104. Moreover, the surrounding sidewall 110 includes a first inwardly extending protrusion 116 that resides about one-third of the way between the face wall 108 and the rim 114 and a second inwardly extending protrusion 118 that resides about two-thirds of the way between the face wall 108 and the rim 114. A preferred method of forming the protrusions 116, 118 is by a swaging process. The protrusions 116, 118 can be an endless annular structure or they can be discontinuous, residing at spaced locations along the perimeter of the sidewall 110.

A first internal partition plate 120 is supported on the first protrusion 116, preferably on a side thereof so that the protrusion resides between the plate 120 and face wall 108. If desired; however, the first partition plate 120 is supported on the protrusion 116 so that the plate is intermediate the protrusion and the face wall. Similarly, a second internal partition plate 122 is supported on the second protrusion 118, preferably on a side thereof so that the protrusion resides between the plate 122 and face wall 108. If desired; however, the second partition plate 122 is supported on the protrusion 118 so that the plate is intermediate the protrusion and the face wall. In any event, the partition plates 120, 122 are secured in place by welds, preferably by laser or resistance spot welding (not shown).

Lid or cover plate 106 is a plate-shaped member that is supported on the rim 114 to thereby close the open end of the container 104. Preferably, the outer edge of cover plate 106 is aligned with the edge 114A of the outwardly extending rim 114. While not shown in FIG. 3, the cover plate 106 is secured to the rim 114 by a weld, which is preferably a laser weld.

In that manner, the casing 102 provides a first capacitor enclosure 124 delineated as the area bounded by the face wall 108, surrounding sidewall 104 and first partition plate 120, a second capacitor enclosure 126 delineated as the area bounded by the first partition plate 120, surrounding sidewall 104 and the second partition plate 122, and a third capacitor enclosure 128 delineated as the area bounded by the second partition plate 122, surround sidewall 104 and the cover plate 106.

A third anodized anode 130 including an extending lead 132 and cathode active material 16 supported on the second plate 122 and cover plate 106 are housed in the third capacitor enclosure 128. The anode and cathode materials are prevented from contacting each other by a separator envelope 134 surrounding the anode 130. The anode 130 and cathode 16 are contacted by a suitable working electrolyte (not shown) and a seal and insulator structure 136, similar to those previously described, electrically isolates the lead 132 from the equipotential casing 102. Finally, FIG. 3 illustrates that the respective anode leads 40, 42 and 132 are unconnected from each other. However, that is by way of example only. If desired, these leads can be electrically connected in parallel as described for leads 40, 42 with respect to FIG. 2.

Moreover, while the capacitor 100 embodiment shown in FIG. 3 has three capacitor enclosures 124, 126 and 128, that is by way of example only. Those skilled in the art will readily understand that a fourth, fifth and more capacitor enclosures, each housing a respective anode and cathode can be provided in the casing 102. The number of capacitor enclosures is only limited by the particular application in which the capacitor is intended to be used as a power source.

Although several embodiments of the invention have been described in detail, for purposes of illustration, various modifications of each may be made without departing from the spirit and scope of the invention. Accordingly, the invention is not to be limited, except as by the appended claims.

What is claimed is:

1. A capacitor, which comprises:
  a) a casing, comprising:
    i) a container comprising a face wall extending to a surrounding sidewall, the surrounding sidewall extending to a annular edge defining an open end of the container, wherein an inwardly extending protrusion is located intermediate the face wall and the annular edge at the container open end;
    ii) a partition plate supported on the protrusion to thereby provide a first capacitor enclosure bounded by the face wall, the surrounding sidewall and the partition plate; and
    iii) a cover plate secured to the annular edge to close the open end of the container and thereby provide a second capacitor enclosure bounded by the partition plate, the surrounding sidewall and the cover plate; and
  b) a cathode active material residing in electrical contact with:

i) at least one of the face wall and the partition plate inside the first capacitor enclosure; and
ii) at least one of the partition plate and the cover plate inside the second capacitor enclosure;
c) at least one anode residing in each of the first and second capacitor enclosures and facing the cathode active material;
d) a separator intermediate the anode and cathode in both of the first and second capacitor enclosures;
e) a first insulative seal supported by the casing to electrically isolate a first lead for the first anode housed in the first capacitor enclosure from the casing;
f) a second insulative seal supported by the casing to electrically isolate a second lead for the second anode housed in the second capacitor enclosure from the casing, the casing serving as a terminal for the cathode active material; and
g) a working electrolyte provided in the first and second capacitor enclosures in contact with the first and second anodes and the cathode active material.

2. The capacitor of claim 1 wherein the inwardly extending protrusion is either an endless annular protrusion or, discontinuous, residing at spaced locations around a perimeter of the surrounding sidewall.

3. The capacitor of claim 1 wherein the inwardly extending protrusion is characterized as having been formed in a swaging process.

4. The capacitor of claim 1 wherein:
i) the first insulative seal comprises a first ferrule supported by the surrounding sidewall; and
ii) the second insulative seal comprises a second ferrule supported by at least one of the surrounding sidewall and the cover plate,
iii) wherein at least one of the first and second ferrules supports a sealing glass contacting the respective first and second anode lead.

5. The capacitor of claim 1 wherein:
i) the first insulative seal comprises a first ferrule supported by the surrounding sidewall; and
ii) the second insulative seal comprises a second ferrule supported by at least one of the surrounding sidewall and the cover plate,
iii) wherein at least one of the first and second ferrules supports a polymeric material, but not a sealing glass, contacting the respective first and second anode lead.

6. The capacitor of claim 1 wherein the cover plate is a planar, plate shaped member aligned substantially parallel to the face wall of the container.

7. The capacitor of claim 1 wherein the surrounding sidewall meets an outwardly extending annular rim at the open end of the container, and the cover plate is supported on the annular rim.

8. The capacitor of claim 7 wherein a first outer edge of the annular rim is aligned with a second outer edge of the cover plate supported on the annular rim.

9. The capacitor of claim 1 wherein the first and second anodes are sintered tantalum pellets that are characterized as having been anodized to a formation voltage that is greater than zero up to 550 V.

10. The capacitor of claim 1 wherein the cathode active material is selected from the group consisting of ruthenium, cobalt, manganese, molybdenum, tungsten, tantalum, iron, niobium, iridium, titanium, zirconium, hafnium, rhodium, vanadium, osmium, palladium platinum, nickel, lead, gold, silver, cobalt, and mixtures thereof.

11. The capacitor of claim 1 wherein the anode is selected from the group consisting of tantalum, aluminum, titanium, niobium, zirconium, hafnium, silicon, germanium, and mixtures thereof.

12. The capacitor of claim 1 wherein the first anode in the first capacitor enclosure is intermediate and facing the cathode active material contacted to an inner surface of the face wall and a first inner surface of the partition plate, and wherein the second anode in the second capacitor enclosure is intermediate and facing the cathode active material contacted to a second inner surface of the partition plate and an inner surface of the cover plate.

13. The capacitor of claim 1 wherein the first and second anodes are electrically connected in parallel outside the casing.

14. A capacitor, which comprises:
a) a casing, comprising:
i) a container comprising a face wall extending to a surrounding sidewall, the surrounding sidewall extending to a annular edge defining an open end of the container, wherein the surrounding sidewall is provided with a first inwardly extending protrusion and a second inwardly extending protrusion, the first protrusion being intermediate the face wall and the second protrusion and the second protrusion being intermediate the first protrusion and the annular edge at the container open end;
ii) a first partition plate supported on the first protrusion to thereby provide a first capacitor enclosure bounded by the face wall, the surrounding sidewall and the first partition plate;
iii) a second partition plate supported on the second protrusion to thereby provide a second capacitor enclosure bounded by the first partition plate, the surrounding sidewall and the second partition plate; and
iv) a cover plate secured to the annular edge to close the open end of the container and thereby provide a third capacitor enclosure bounded by the second partition plate, the surrounding sidewall and the cover plate; and
b) a cathode active material residing in electrical contact with:
i) at least one of the face wall and the first partition plate inside the first capacitor enclosure;
ii) at least one of the first partition plate and the second partition plate inside the second capacitor enclosure; and
iii) at least one of the second partition plate and the cover plate inside the third capacitor enclosure; and
c) at least one anode residing in each of the first, second and third capacitor enclosures and facing the cathode active material;
d) a separator intermediate the anode and cathode in the first, second and third capacitor enclosures;
e) a first insulative seal supported by the casing to electrically isolate a first lead for the first anode housed in the first capacitor enclosure from the casing;
f) a second insulative seal supported by the casing to electrically isolate a second lead for the second anode housed in the second capacitor enclosure from the casing;
g) a third insulative seal supported by the casing to electrically isolate a third lead for the third anode housed in the third capacitor enclosure from the casing, the casing serving as a terminal for the cathode active material; and h) a working electrolyte provided in the first, second and third capacitor enclosures in contact with the first, second and third anodes and the cathode active material.

15. The capacitor of claim 14 wherein the first and second protrusions are individually either an endless annular protrusion or, discontinuous, residing at spaced locations around a perimeter of the surrounding sidewall.

16. The capacitor of claim 14 wherein the first and second protrusions are characterized as having been formed in a swaging process.

* * * * *